US009282736B2

(12) United States Patent
Kostansek et al.

(10) Patent No.: US 9,282,736 B2
(45) Date of Patent: *Mar. 15, 2016

(54) OIL FORMULATIONS WITH THICKENERS

(71) Applicant: Agrofresh, Inc., Collegeville, PA (US)

(72) Inventors: Edward Charles Kostansek, Buckingham, PA (US); Richard Martin Jacobson, Chalfont, PA (US)

(73) Assignee: AGROFRESH INC., Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/455,374

(22) Filed: Aug. 8, 2014

(65) Prior Publication Data

US 2015/0005171 A1    Jan. 1, 2015

Related U.S. Application Data

(63) Continuation of application No. 14/014,950, filed on Aug. 30, 2013, now Pat. No. 9,012,515, which is a continuation-in-part of application No. 13/531,884, filed on Jun. 25, 2012, now abandoned, which is a continuation of application No. 12/220,407, filed on Jul. 24, 2008, now Pat. No. 8,247,459.

(60) Provisional application No. 60/963,297, filed on Aug. 3, 2007, provisional application No. 61/710,019, filed on Oct. 5, 2012.

(51) Int. Cl.
| | |
|---|---|
| *A61K 31/015* | (2006.01) |
| *A61K 9/48* | (2006.01) |
| *A61K 9/14* | (2006.01) |
| *A01N 25/04* | (2006.01) |
| *A01N 43/16* | (2006.01) |
| *A01N 3/00* | (2006.01) |
| *A01N 25/02* | (2006.01) |
| *A01N 27/00* | (2006.01) |

(52) U.S. Cl.
CPC ............ *A01N 25/04* (2013.01); *A01N 3/00* (2013.01); *A01N 25/02* (2013.01); *A01N 27/00* (2013.01); *A01N 43/16* (2013.01)

(58) Field of Classification Search
None
See application file for complete search history.

(56) References Cited

U.S. PATENT DOCUMENTS

| | | | |
|---|---|---|---|
| 6,017,849 A | 1/2000 | Daly et al. | |
| 6,313,068 B1 | 11/2001 | Daly et al. | |
| 6,426,319 B1 | 7/2002 | Kostansek et al. | |
| 6,444,619 B1 | 9/2002 | Kostansek et al. | |
| 6,548,448 B2 | 4/2003 | Kostansek et al. | |
| 8,247,459 B2 * | 8/2012 | Kostansek | A01N 3/00 424/451 |
| 8,461,086 B2 | 6/2013 | Chang et al. | |
| 8,541,344 B2 | 9/2013 | Kostansek et al. | |
| 9,012,515 B2 * | 4/2015 | Kostansek | A01N 3/00 424/451 |
| 2002/0043730 A1 | 4/2002 | Chong et al. | |
| 2003/0083209 A1 | 5/2003 | Moodycliffe | |
| 2004/0211316 A1 | 10/2004 | Collins | |
| 2005/0261131 A1 | 11/2005 | Basel et al. | |
| 2005/0261132 A1 | 11/2005 | Kostansek et al. | |
| 2005/0272615 A1 | 12/2005 | Bitler | |
| 2006/0160704 A1 | 7/2006 | Basel et al. | |
| 2007/0105722 A1 | 5/2007 | Basel et al. | |
| 2007/0117720 A1 | 5/2007 | Jacobson et al. | |
| 2009/0035380 A1 | 2/2009 | Kostansek et al. | |
| 2010/0144533 A1 | 6/2010 | Baier et al. | |
| 2011/0092369 A1 | 4/2011 | Chang et al. | |
| 2012/0264606 A1 | 10/2012 | Kostansek et al. | |
| 2013/0345059 A1 | 12/2013 | Kostansek et al. | |

FOREIGN PATENT DOCUMENTS

| | | |
|---|---|---|
| JP | 58058139 | 4/1983 |
| JP | 03178906 | 8/1991 |
| WO | 97/09882 | 3/1997 |
| WO | 2011/109144 | 9/2011 |
| WO | 2011/156388 | 12/2011 |
| WO | 2014/055208 | 4/2014 |

OTHER PUBLICATIONS

PCT International Search Report and Written Opinion for PCT/US2013/059201, mailed Apr. 28, 2014.
Unisource Energy Inc., Specialty Aliphatic Solvent Typical Properties, Mar. 2000, available at http://unisource-energy.com/msdsdatasheets/UNIPARSH210ASds.pdf, accessed on Mar. 12, 2014, UNIPAR SH 210: CAS No. 64742-47-8.

* cited by examiner

*Primary Examiner* — Alton Pryor
(74) *Attorney, Agent, or Firm* — Barnes & Thornburg LLP

(57) ABSTRACT

This invention is based on unexpected effect of at least one thickener to maintain suspension or dispersion of solid particles in an oil medium. Such effect of thickener enables significant higher weight ratio of solid particles in such suspension composition as compared to previously known compositions. As a consequence, the suspension compositions provided herein enable more active ingredient in the solid particle to be present in a fixed volume or weight of such composition as compared to previously known compositions. One advantage of the suspension composition provided herein can be for aerial spraying of active ingredient such as herbicides, insecticides, or other growth regulating compounds.

10 Claims, No Drawings

OIL FORMULATIONS WITH THICKENERS

CROSS-REFERENCE TO RELATED APPLICATIONS

This application is a continuation of U.S. application Ser. No. 14/014,950, filed Aug. 30, 2013, which claims priority under 35 U.S.C. §119 to U.S. Provisional Application Ser. No. 61/710,019, filed Oct. 5, 2012, both of which applications are hereby incorporated by reference in their entireties. U.S. application Ser. No. 14/014,950, filed Aug. 30, 2013, also claims priority as a continuation-in-part of U.S. application Ser. No. 13/531,884, filed Jun. 25, 2012, which is a continuation of U.S. application Ser. No. 12/220,407 filed on Jul. 24, 2008, now U.S. Pat. No. 8,247,459, which claims priority under 35 U.S.C. §119 to U.S. Provisional Application Ser. No. 60/963,297, filed on Aug. 3, 2007; the contents of which are hereby incorporated by reference in their entireties.

BACKGROUND OF THE INVENTION

For the use of cyclopropenes, the cyclopropene is often in the form of a complex with a molecular encapsulating agent. Such a complex is useful, for example, for use in treating plants or plant parts by contacting the plants or plant parts with the complex in order to bring about contact between the plants or plant parts and the cyclopropene. Such treatment of plants or plant parts is often effective at desirably interrupting one or more ethylene-mediated process in the plants or plant parts. For example, such treatment of plant parts can sometimes desirably delay unwanted ripening. For another example, such treatment of crop plants prior to harvest can sometimes improve the yield of the crop.

U.S. Pat. No. 6,313,068 discloses grinding and milling of dried powder of a complex of cyclodextrin and methylcyclopropene.

It is often useful to dissolve or suspend particles of such a complex in a liquid. However, if water is the liquid, it is sometimes found that contact between the water and the particles of the complex causes release of the cyclopropene from the complex earlier than desired, and some or all of the cyclopropene is thus lost to the surroundings or destroyed by a chemical reaction or a combination thereof. Therefore, it is often desirable to suspend such particles in oil. However, in the past, attempts to suspend such particles in oil have found that such particles could not be suspended effectively in oil, often because the suspensions could not be sprayed properly, or because the suspensions had too high viscosity at reasonable concentration of particles, or because the suspensions were not stable, or the suspension settled or creamed, or because the suspensions had some combination of these problems. The object of the present invention is to provide suspensions in oil of particles containing cyclopropene complex that solve one or more of these problems.

SUMMARY OF THE INVENTION

This invention is based on unexpected effect of at least one thickener to maintain suspension or dispersion of solid particles in an oil medium. Such effect of thickener enables significant higher weight ratio of solid particles in such suspension composition as compared to previously known compositions. As a consequence, the suspension compositions provided herein enable more active ingredient in the solid particle to be present in a fixed volume or weight of such composition as compared to previously known compositions. One advantage of the suspension composition provided herein can be for aerial spraying of active ingredient such as herbicides, insecticides, or growth regulating compounds. Other advantages of the suspension composition provided herein include slow release of cyclopropene, and lower payload weight for airplanes and helicopters for aerial applications.

Provided are suspension of cyclopropene/cyclodextrin complexes in a hydrophobic fluid with adjuvants which can form a system for the controlled delivery of cyclopropenes.

In one aspect, provided is a composition comprising an oil medium and at least one thickener, wherein the composition is a suspension of solid particles in the oil medium, and the solid particles comprise cyclopropene and molecular encapsulating agent.

In one embodiment, the suspension does not settle for at least two weeks, at least four weeks, at least eight weeks, at least twenty weeks, or at least forty weeks. In another embodiment, the oil medium is selected from the group consisting of white mineral oil, hydrotreated middle petroleum distillate, hydrotreated light petroleum distillate, and combinations thereof. In a further embodiment, the white mineral oil comprises Blandol and/or Klearol. In another further embodiment, the hydrotreated middle petroleum distillate comprises Conosol 260, Unipar SH 260 CC, and/or Isopar V. In another further embodiment, the hydrotreated light petroleum distillate comprises Unipar SH 210 AS and/or Isopar M.

In one embodiment, the cyclopropene compound is of the formula:

$$\triangleright\!\!-\!\!R$$

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In another embodiment, the cyclopropene compound is of the formula:

$$R^1\!\!-\!\!\overset{R^3\quad R^4}{\underset{}{\triangle}}\!\!-\!\!R^2$$

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

In one embodiment, the cyclopropene comprises 1-methylcyclopropene (1-MCP). In another embodiment, the molecular encapsulating agent is selected from the group consisting of substituted cyclodextrins, unsubstituted cyclodextrins, and combinations thereof. In a further embodiment, the molecular encapsulating agent comprises alpha-cyclodextrin.

In one embodiment, the solid particles comprise at least 5%, at least 10%, at least 20%, at least 30%, at least 40%, at least 50%, or at least 60% by weight of the composition. In another embodiment, the solid particles comprise 10-20%, 10-30%, 10-40%, 10-50%, 10-60%, 20-40%, 30-60%, or 40-60% by weight of the composition. In another embodiment, the composition comprises at least 5%, at least 10%, at least 20%, at least 30%, at least 40%, at least 50%, or at least 60% by weight of a complex of 1-methylcyclopropene (1-MCP) and alpha-cyclodextrin. In another embodiment, the composition comprises 10-20%, 10-30%, 10-40%, 10-50%, 10-60%, 20-40%, 30-60%, or 40-60% by weight of a complex of 1-methylcyclopropene (1-MCP) and alpha-cyclodextrin.

In one embodiment, the composition comprises at least 1%, at least 3%, at least 5%, at least 10%, at least 15%, at least 20%, at least 30%, at least 40%, or at least 50% by weight the at least one thickener. In another embodiment, the composition comprises 1-20%, 1-30%, 1-40%, 1-50%, 5-20%, 5-40%, 10-50%, or 20-50% by weight the at least one thickener. In another embodiment, the at least one thickener comprises a cellulose-based thickener. In another embodiment, the at least one thickener comprises a polymeric thickener. In a further embodiment, the polymeric thickener is formed from at least one of acrylates, alkylacrylates, and anhydrides. In another further embodiment, the polymeric thickener comprises at least one component selected from the group consisting of polypropylene, polyisoprene, polybutadiene, poly(styrene-butadiene), poly(styrene-ethylene/propylene), poly(ethylene-propylene-diene), polyurethane, polymethacrylate, polyisobutylene, poly(isobutylene-succinic acid), poly(isobutylene-succinic acid-polyacrylamide), polyurea, polyethylene, and combinations thereof.

In another embodiment, the polymeric thickener comprises a first component and a second component, with the first component having a higher weight average molecular weight than the second component. In a further embodiment, the weight ratio of the first component to the second component is at least 1:5, at least 1:10, at least 1:20, at least 1:30, at least 1:40, or at least 1:50. In another further embodiment, the weight ratio of the first component to the second component is between 1:5 and 1:20; between 1:10 to 1:40, or between 1:5 and 1:50. In another embodiment, the polymeric thickener does not comprise ethylene propylene norbornadiene copolymer. In a further embodiment, such ethylene propylene norbornadiene copolymer does not comprise Nordel IP3745P. In another embodiment, the polymeric thickener does not comprise styrene ethylene/propylene copolymer. In a further embodiment, such styrene ethylene/propylene copolymer does not comprise Septon 1020 or Septon 1001.

In another aspect, provided is a method of preparing a suspension composition comprising (a) placing materials comprising complex comprising cyclopropene and molecular encapsulating agent, an oil medium, and at least one thickener into a media mill; and (b) milling the materials into a composition comprising solid particles.

In one embodiment, the suspension composition does not settle for at least two weeks, at least four weeks, at least eight weeks, at least twenty weeks, or at least forty weeks. In another embodiment, the oil medium is selected from the group consisting of white mineral oil, hydrotreated middle petroleum distillate, hydrotreated light petroleum distillate, and combinations thereof. In a further embodiment, the white mineral oil comprises Blandol and/or Klearol. In another further embodiment, the hydrotreated middle petroleum distillate comprises Conosol 260, Unipar SH 260 CC, and/or Isopar V. In another further embodiment, the hydrotreated light petroleum distillate comprises Unipar SH 210 AS and/or Isopar M.

In one embodiment, the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_1$-8 alkyl. In another embodiment, R is methyl.

In another embodiment, the cyclopropene compound is of the formula:

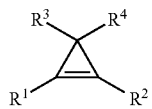

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

In one embodiment, the cyclopropene comprises 1-methylcyclopropene (1-MCP). In another embodiment, the molecular encapsulating agent is selected from the group consisting of substituted cyclodextrins, unsubstituted cyclodextrins, and combinations thereof. In a further embodiment, the molecular encapsulating agent comprises alpha-cyclodextrin.

In one embodiment, the composition comprises at least 5%, at least 10%, at least 20%, at least 30%, at least 40%, at least 50%, or at least 60% by weight a complex of 1-methylcyclopropene (1-MCP) and alpha-cyclodextrin. In another embodiment, the composition comprises 10-20%, 10-30%, 10-40%, 10-50%, 10-60%, 20-40%, 30-60%, or 40-60% by weight a complex of 1-methylcyclopropene (1-MCP) and alpha-cyclodextrin.

In one embodiment, the composition comprises at least 1%, at least 3%, at least 5%, at least 10%, at least 15%, at least 20%, at least 30%, at least 40%, or at least 50% by weight the at least one thickener. In another embodiment, the composition comprises 1-20%, 1-30%, 1-40%, 1-50%, 5-20%, 5-40%, 10-50%, or 20-50% by weight the at least one thickener. In another embodiment, the at least one thickener comprises a cellulose-based thickener. In another embodiment, the at least one thickener comprises a polymeric thickener. In a further embodiment, the polymeric thickener is formed from at least one of acrylates, alkylacrylates, and anhydrides. In another further embodiment, the polymeric thickener comprises at least one component selected from the group consisting of polypropylene, polyisoprene, polybutadiene, poly(styrene-butadiene), poly(styrene-ethylene/propylene), poly(ethylene-propylene-diene), polyurethane, polymethacrylate, polyisobutylene, poly(isobutylene-succinic acid), poly(isobutylene-succinic acid-polyacrylamide), polyurea, polyethylene, and combinations thereof.

In another embodiment, the polymeric thickener comprises a first component and a second component, with the first component having a higher weight average molecular weight than the second component. In a further embodiment, the weight ratio of the first component to the second component is at least 1:5, at least 1:10, at least 1:20, at least 1:30, at least 1:40, or at least 1:50. In another further embodiment, the weight ratio of the first component to the second component is between 1:5 and 1:20; between 1:10 to 1:40, or between 1:5 and 1:50. In another embodiment, the polymeric thickener does not comprise ethylene propylene norbornadiene copolymer. In a further embodiment, such ethylene propylene norbornadiene copolymer does not comprise Nordel IP3745P. In another embodiment, the polymeric thickener does not comprise styrene ethylene/propylene copolymer. In a further embodiment, such styrene ethylene/propylene copolymer does not comprise Septon 1020 or Septon 1001.

DETAILED DESCRIPTION OF THE INVENTION

When a compound is described herein as being present as a gas in an atmosphere at a certain concentration using the unit "ppm," the concentration is given as parts by volume of that compound per million parts by volume of the atmosphere. Similarly, "ppb" denotes parts by volume of that compound per billion parts by volume of the atmosphere.

The present invention involves the use of one or more cyclopropene compound. As used herein a cyclopropene compound is any compound with the formula

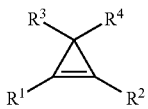

where each $R^1$, $R^2$, $R^3$ and $R^4$ is independently selected from the group consisting of H and a chemical group of the formula:

$-(L)_n-Z$ where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6.

Independently, in any one R group the total number of non-hydrogen atoms is 50 or less.

Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent. It is contemplated that such substituted groups may be made by any method, including but not limited to making the unsubstituted form of the chemical group of interest and then performing a substitution. Suitable substituents include, for example, alkyl, alkenyl, acetylamino, alkoxy, alkoxyalkoxy, alkoxycarbonyl, alkoxyimio, carboxy, halo, haloalkoxy, hydroxy, alkylsulfonyl, alkylthio, trialkylsilyl, dialkylamino, and combinations thereof. An additional suitable substituent, which, if present, may be present alone or in combination with another suitable substituent, is $-(L)_m-Z$ where m is 0 to 8, and where L and Z are defined herein above. If more than one substituent is present on a single chemical group of interest, each substituent may replace a different hydrogen atom, or one substituent may be attached to another substituent, which in turn is attached to the chemical group of interest, or a combination thereof.

Among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., aromatic or non-aromatic cyclic groups with at least one heteroatom in the ring).

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups. Suitable substituents are those described herein above. In some embodiments, one or more substituted aryl group is used in which at least one substituent is one or more of alkenyl, alkyl, alkynyl, acetylamino, alkoxyalkoxy, alkoxy, alkoxycarbonyl, carbonyl, alkylcarbonyloxy, carboxy, arylamino, haloalkoxy, halo, hydroxy, trialkylsilyl, dialkylamino, alkylsulfonyl, sulfonylalkyl, alkylthio, thioalkyl, arylaminosulfonyl, and haloalkylthio.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, for example, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from the substituents described herein above. Also suitable are embodiments in which G is a carbocyclic ring system.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there may be 1, 2, or 3 substituents. Independently, also among embodiments in which G is substituted phenyl are embodiments, for example, in which the substituents are independently selected from methyl, methoxy, and halo.

Also contemplated are embodiments in which $R^3$ and $R^4$ are combined into a single group, which is attached to the number 3 carbon atom of the cyclopropene ring by a double bond. Some of such compounds are described in US Patent Publication 2005/0288189.

In some embodiments, one or more cyclopropenes are used in which one or more of $R^1$, $R^2$, $R^3$, and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$, and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$, and $R^4$ is a structure that has no halogen atom substituent. Independently, in some embodiments, one or more of $R^1$, $R^2$, $R^3$, and $R^4$ is a structure that has no substituent that is ionic.

In some embodiments, one or more of $R^1$, $R^2$, $R^3$, and $R^4$ is hydrogen or ($C_1$-$C_{10}$) alkyl. In some embodiments, each of $R^1$, $R^2$, $R^3$, and $R^4$ is hydrogen or ($C_1$-$C_8$) alkyl. In some embodiments, each of $R^1$, $R^2$, $R^3$, and $R^4$ is hydrogen or ($C_1$-$C_4$) alkyl. In some embodiments, each of $R^1$, $R^2$, $R^3$, and $R^4$ is hydrogen or methyl. In some embodiments, $R^1$ is ($C_1$-$C_4$) alkyl and each of $R^2$, $R^3$, and $R^4$ is hydrogen. In some embodiments, $R^1$ is methyl and each of $R^2$, $R^3$, and $R^4$ is hydrogen, and the cyclopropene compound is known herein as 1-methylcycplopropene or "1-MCP."

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this invention may be prepared by any method. Some suitable methods of preparation of cyclopropenes are the processes disclosed in U.S. Pat. Nos. 5,518,988 and 6,017,849.

The composition of the present invention may include at least one molecular encapsulating agent. In some embodiments, at least one molecular encapsulating agent encapsulates one or more cyclopropene or a portion of one or more cyclopropene. A complex that contains a cyclopropene molecule or a portion of a cyclopropene molecule encapsulated in a molecule of a molecular encapsulating agent is known herein as a "cyclopropene complex."

In some embodiments, at least one cyclopropene complex is present that is an inclusion complex. In such an inclusion complex, the molecular encapsulating agent forms a cavity, and the cyclopropene or a portion of the cyclopropene is located within that cavity. In some of such inclusion complexes, there is no covalent bonding between the cyclopropene and the molecular encapsulating agent. Independently, in some of such inclusion complexes, there is no ionic bonding between the cyclopropene and the molecular encapsulating complex, whether or not there is any electrostatic attraction between one or more polar moiety in the cyclopropene and one or more polar moiety in the molecular encapsulating agent.

Independently, in some of such inclusion complexes, the interior of the cavity of the molecular encapsulating agent is substantially apolar or hydrophobic or both, and the cyclopropene (or the portion of the cyclopropene located within that cavity) is also substantially apolar or hydrophobic or both. While the present invention is not limited to any particular theory or mechanism, it is contemplated that, in such apolar cyclopropene complexes, van der Waals forces, or hydrophobic interactions, or both, cause the cyclopropene molecule or portion thereof to remain within the cavity of the molecular encapsulating agent.

The cyclopropene molecular encapsulation agent complexes can be prepared by any means. In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which cyclopropene is encapsulated in a molecular encapsulating agent, the cyclopropene gas is bubbled through a solution of molecular encapsulation agent in water, from which the complex first precipitates and is then isolated by filtration. In some embodiments, complexes are made by the above method and, after isolation, are dried and stored in solid form, for example as a powder, for later addition to useful compositions.

The amount of molecular encapsulating agent can usefully be characterized by the ratio of moles of molecular encapsulating agent to moles of cyclopropene. In some embodiments, the ratio of moles of molecular encapsulating agent to moles of cyclopropene may be 0.1 or larger; 0.2 or larger; 0.5 or larger; or 0.9 or larger. Independently, in some of such embodiments, the ratio of moles of molecular encapsulating agent to moles of cyclopropene may be 2 or lower; or 1.5 or lower.

Suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments, the encapsulating agent is alpha-cyclodextrin, beta-cyclodextrin, gamma-cyclodextrin, or a mixture thereof. In some embodiments of the invention, alpha-cyclodextrin is used. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof can also be utilized pursuant to the present invention. Some cyclodextrins are available, for example, from Wacker Biochem Inc., Adrian, Mich. or Cerestar USA, Hammond, Ind., as well as other vendors.

In the practice of the present invention, one or more oils are used. As used herein, an "oil" is a compound that is liquid at 25° C. and 1 atmosphere pressure and that has a boiling point at 1 atmosphere pressure of 30° C. or higher. As used herein, "oil" does not include water, does not include surfactants (as described herein), and does not include dispersants (as described herein).

In some embodiments, one or more oil may be used that has boiling point of 50° C. or higher; or 75° C. or higher; or 100° C. or higher. In some embodiments, every oil that is used has boiling point of 50° C. or higher. In some embodiments, every oil that is used has boiling point of 75° C. or higher. In some embodiments, every oil that is used has boiling point of 100° C. or higher. Independently, in some of the embodiments that use oil, one or more oil may be used that has an average molecular weight of 100 or higher; or 200 or higher; or 500 or higher. In some embodiments, every oil that is used has average molecular weight of 100 or higher. In some embodiments, every oil that is used has average molecular weight of 200 or higher. In some embodiments, every oil that is used has average molecular weight of 500 or higher.

An oil may be either a hydrocarbon oil (i.e., an oil whose molecule contains only atoms of carbon and hydrogen) or a non-hydrocarbon oil (i.e., an oil whose molecule contains at least at least one atom that is neither carbon nor hydrogen).

Some suitable hydrocarbon oils are, for example, straight, branched, or cyclic alkane compounds with 6 or more carbon atoms. Some other suitable hydrocarbon oils, for example, have one or more carbon-carbon double bond, one or more carbon-carbon triple bond, or one or more aromatic ring, possibly in combination with each other and/or in combination with one or more alkane group. Some suitable hydrocarbon oils are obtained from petroleum distillation and contain a mixture of compounds, along with, in some cases, impurities. Hydrocarbon oils obtained from petroleum distillation may contain a relatively wide mixture of compositions or may contain relatively pure compositions. In some embodiments, hydrocarbon oils are used that contain 6 or more carbon atoms. In some embodiments, hydrocarbon oils are used that contain 18 or fewer carbon atoms. In some embodiments, every hydrocarbon oil that is used contains 18 or fewer carbon atoms. In some embodiments, every hydrocarbon oil that is used contains 6 or more carbon atoms. Some suitable hydrocarbon oils include, for example, hexane, decane, dodecane, hexadecane, diesel oil, hydrotreated light petroleum distillates, hydrotreated medium petroleum distillates, refined paraffinic oil (e.g., Ultrafine™ spray oil from Sun Company), and mixtures thereof. In some embodiments, every oil that is used is a hydrocarbon oil.

Among embodiments that use non-hydrocarbon oil, some suitable non-hydrocarbon oils are, for example, fatty non-hydrocarbon oils. "Fatty" means herein any compound that contains one or more residues of fatty acids. Fatty acids are long-chain carboxylic acids, with chain length of at least 4 carbon atoms. Typical fatty acids have chain length of 4 to 18 carbon atoms, though some have longer chains. Linear, branched, or cyclic aliphatic groups may be attached to the long chain. Fatty acid residues may be saturated or unsaturated, and they may contain functional groups, including for example alkyl groups, epoxide groups, halogens, sulfonate groups, or hydroxyl groups, which are either naturally occurring or that have been added. Some suitable fatty non-hydrocarbon oils are, for example, fatty acids; esters of fatty acids; amides of fatty acids; dimers, trimers, oligomers, or polymers thereof; and mixtures thereof.

Some of the suitable fatty non-hydrocarbon oils are, for example, esters of fatty acids. Such esters include, for example, glycerides of fatty acids. Glycerides are esters of fatty acids with glycerol, and they may be mono-, di-, or triglycerides. A variety of triglycerides are found in nature. Most of the naturally occurring triglycerides contain residues of fatty acids of several different lengths and/or compositions. Some suitable triglycerides are found in animal sources such as, for example, dairy products, animal fats, or fish. Further examples of suitable triglycerides are oils found in plants, such as, for example, coconut, palm, cottonseed, olive, tall, peanut, safflower, sunflower, corn, soybean, linseed, tung, castor, canola, citrus seed, cocoa, oat, palm, palm kernel, rice bran, cuphea, or rapeseed oil.

Among the suitable triglycerides, independent of where they are found, are those, for example, that contain at least one fatty acid residue that has 14 or more carbon atoms. Some suitable triglycerides have fatty acid residues that contain 50% or more by weight, based on the weight of the residues, fatty acid residues with 14 or more carbon atoms, or 16 or more carbon atoms, or 18 or more carbon atoms. One example of a suitable triglyceride is soybean oil.

Suitable fatty non-hydrocarbon oils may be synthetic or natural or modifications of natural oils or a combination or mixture thereof. Among suitable modifications of natural oils are, for example, alkylation, hydrogenation, hydroxylation, alkyl hydroxylation, alcoholysis, hydrolysis, epoxidation, halogenation, sulfonation, oxidation, polymerization, and combinations thereof. In some embodiments, alkylated (including, for example, methylated and ethylated) oils are used. One suitable modified natural oil is methylated soybean oil.

Also among the suitable fatty non-hydrocarbon oils are self-emulsifying esters of fatty acids.

Another group of suitable non-hydrocarbon oils is the group of silicone oils. Silicone oil is an oligomer or polymer that has a backbone that is partially or fully made up of —Si—O— links. Silicone oils include, for example, polydimethylsiloxane oils. Polydimethylsiloxane oils are oligomers or polymers that contain units of the form

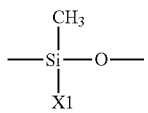

where at least one of the units has X1=CH₃. In other units, X1 may be any other group capable of attaching to Si, including, for example, hydrogen, hydroxyl, alkyl, alkoxy, hydroxyalkyl, hydroxyalkoxy, alkylpolyalkoxyl, substituted versions thereof, or combinations thereof. Substituents may include, for example, hydroxyl, alkoxyl, polyethoxyl, ether linkages, ester linkages, amide linkages, other substituents, or any combination thereof. In some embodiments, every oil that is used is a silicone oil.

In some suitable polydimethylsiloxane oils, all X1 groups are groups that are not hydrophilic. In some suitable polydimethylsiloxane oils, all X1 groups are alkyl groups. In some suitable polydimethylsiloxane oils, all X1 groups are methyl. In some embodiments, every silicone oil is a polydimethylsiloxane oil in which all X1 groups are methyl. In some suitable polydimethylsiloxanes, at least one unit has an X1 group that is not methyl; if more than one non-methyl X1 unit is present, the non-methyl X1 units may be the same as each other, or two or more different non-methyl X1 units may be present. Polydimethylsiloxane oils may be end-capped with any of a wide variety of chemical groups, including, for example, hydrogen, methyl, other alkyl, or any combination thereof. Also contemplated are cyclic polydimethylsiloxane oils. Mixtures of suitable oils are also suitable.

The practice of the present invention involves particles suspended in an oil medium. The oil medium may be any of the oils described herein above. By "suspended" herein is meant that the particles are insoluble or only slightly soluble in the oil and that the particles are distributed throughout the oil, which forms a continuous medium around the particles. The system of particles suspended in oil is known herein as a "suspension." The suspensions of the present invention are stable; that is, under normal conditions of 25° C., 1 atmosphere pressure, and normal gravity, upon storage for 1 day, most of the particles (at least 80% by weight, based on the total dry weight of the particles) will not settle to the bottom of the container or float to the top of the container. In some embodiments, the amount of particles that settles to the bottom of the container on storage, by weight based on the total dry weight of the particles, is 10% or less, or 5% or less, or 2% or less, or 1% or less. Independently, in some embodiments, suspensions are used that are stable upon storage for 2 days or longer, or 5 days or longer, or 10 days or longer.

The collection of particles can be assessed to determine the size. One suitable method of assessment, for example, is inspection using a microscope. Images of particles, for example, those images obtained in a microscope, may be inspected and assessed by eye, possibly with reference to length standards, or alternatively the images may be inspected and assessed by appropriate image analysis methods, such as, for example, computer programs.

In embodiments in which the particles are not spherical, it is useful to characterize the particles by the largest dimension of each particle. A collection of particles may be characterized by the median value of the largest dimension. That is, half of the particles in the collection, by weight, will have largest dimension that is larger than the median value of the collection. In the practice of the present invention, when the collection of particles suspended in the oil medium is assessed, that median value is 50 micrometers or less. In some embodiments, particles are used in which that median value is 20 micrometers or less; or 10 micrometers or less; or 5 micrometers or less; or 2 micrometers or less.

An independent measure of a particle is the aspect ratio, which is the ratio of the largest dimension of the particle to the smallest dimension of the particle. The aspect ratio is independent of the size of the particle. In some embodiments of the present invention, the collection of particles suspended in oil medium has aspect ratio of 20 or lower; or 10 or lower; or 5 or lower; or 2 or lower.

The particles that are suspended in the oil medium are solid. That is, the particles are partially or fully made of material that is in the solid state. Each particle may or may not be porous or may or may not have one or more void or may or may not have one or more cavity, and each pore or void or cavity (if present) may or may not be partially or fully occupied by material that is solid, liquid, or gas. The system of particles suspended in the oil medium is synonymously known as a "dispersion."

The particles that are suspended in the oil medium may contain cyclopropene and molecular encapsulating agent. In some embodiments, some or all of the cyclopropene that is present in the composition is part of a cyclopropene complex. While the present invention is not limited to any particular theory or model, it is contemplated that most or all of the cyclopropene molecules that are present in the composition are present in the form of molecules that are part of cyclopropene complexes. It is further contemplated that any cyclopropene molecules in the composition that are not part of a cyclopropene complex are present, for example, in solution, adsorbed on an interface, some other location, or a combination thereof. In some embodiments, the amount of cyclopropene that is present as part of a cyclopropene complex, by weight based on the total amount of cyclopropene in the composition may be 80% or more; or 90% or more; or 95% or more; or 99% or more.

In some embodiments of the present invention, the oil medium comprises one or more dispersant. It is contemplated that some or all of the dispersant is dissolved in the oil, that some or all of the dispersant is located on the particle surface (i.e., at the interface between the particle and the oil medium), or a combination thereof. Additionally, it is contemplated that small amounts of dispersant (or none) may be located in one or more other places, such as, for example, at the surface of the oil, on the walls of the container, in a complex with a molecular encapsulating agent, or a combination thereof.

As defined herein, a "dispersant" is a compound that is capable of assisting a solid particle to form a stable suspension in a liquid medium. Most dispersants act by minimizing the ability of the particles to agglomerate making, essentially, larger particles which are more likely to settle (or cream). In some embodiments, suitable dispersants have one or more hydrophilic group. Independently, in some embodiments, suitable dispersants have multiple hydrophobic groups. Some suitable hydrophobic groups include, for example, organic groups with 8 or more consecutive carbon atoms. In some embodiments, hydrophobic groups are present that have 10 or more consecutive carbon atoms. Independent of the number of carbon atoms, such organic groups may be linear, cyclic, branched or a combination thereof. Independently, such organic groups may be hydrocarbons or may be substituted. Independently, such organic groups may be saturated or unsaturated.

Some suitable dispersants have 2 or more hydrophobic groups per molecule, or 3 or more, or 4 or more, or 5 or more. In some embodiments, every dispersant has 4 or more hydrophobic groups per molecule. In some embodiments, every dispersant has 5 or more hydrophobic groups per molecule.

Independent of the nature of the hydrophobic group, some suitable dispersants have one or more hydrophilic group. Some suitable hydrophilic groups include, for example, groups that are capable of ionizing in water over certain ranges of pH, such as, for example, carboxyl groups, sulfate groups, sulfonate groups, and amine groups. Other suitable hydrophilic groups are nonionic. Some suitable nonionic hydrophilic groups include, for example, segments of polymers that, if they existed independently as polymers, would be soluble in water. Such hydrophilic segments of polymers include, for example, polyethylene glycol segments.

In embodiments in which dispersant is used, the molecule of which contains both hydrophobic groups and at least one hydrophilic group, the groups may be attached to the dispersant molecule in any way. For example, some suitable dispersants are block copolymers with at least one block that is a polyethylene glycol segment and at least one block that contains plural hydrophobic groups. One example of a block containing plural hydrophobic groups is segment of poly(12-hydroxystearic acid). Another example of a block containing plural hydrophobic groups is a segment of an alkyd polymer. Alkyd polymers are copolymers of polyols, polybasic acids, and fatty acids or triglyceride oils.

As used herein, a nonionic dispersant is a dispersant in which all of the hydrophilic groups are nonionic. In some embodiments, at least one nonionic dispersant is used. In some embodiments, every dispersant that is used is nonionic.

One useful characteristic of a nonionic molecule is the HLB value, which is defined by the equation $$HLB = 20 * M_H / M$$

where $M_H$ is the molecular mass of the hydrophilic portion of the molecule, and M is the molecular mass of the molecule.

A molecule of interest, whether ionic or nonionic, may be characterized by the acid number (synonymously called "acid value"), which is the milligrams of KOH needed to neutralize the molecule of interest, per gram of the molecule of interest. One method of testing the acid number is shown in ASTM D-7253. It is understood that some details of the test (such as, for example, selection of solvent and/or indicator) may be adapted as necessary for the specific molecule of interest.

In some embodiments in which one or more nonionic dispersant is used, one or more of the dispersants has HLB of higher than 4, or HLB of 5 or higher. Independently, in some embodiments, one or more dispersant is used that has HLB of lower than 8, or HLB of 7 or lower. In some embodiments, every dispersant that is used has HLB that is 5 to 7.

Independent of the HLB value of the dispersant, in some embodiments in which one or more nonionic dispersant is used, one or more of the dispersants has acid number, in units of mg KOH/g, of 10 or lower; or 9 or lower; or 8 or lower. Independently, in some embodiments in which one or more nonionic dispersant is used, one or more of the dispersants has acid number, in units of mg KOH/g, of 2 or higher; or 4 or higher; or 6 or higher. In some embodiments, every dispersant that is used has acid number that is 6 to 8 mg KOH/g.

In some embodiments, one or more dispersant is used that has acid number that is 6 to 8 mg KOH/g or higher, where the same dispersant also has HLB that is 5 to 7.

In some embodiments, one or more surfactant is used. "Surfactant," as used herein, is synonymous with "emulsifier" and means a compound that assists the formation of a stable suspension of oil droplets in water. The molecule of a surfactant compound contains at least one hydrophilic group and at least one hydrophobic group. Surfactants are normally classified according to the nature of the hydrophilic group. Suitable surfactants include, for example, anionic surfactants, cationic surfactants, nonionic surfactants, amphoteric surfactants, and mixtures thereof.

In embodiments in which one or more anionic surfactant is used, some suitable anionic surfactants include, for example, the sulfosuccinates (including, for example, alkaline salts of mono- and dialkyl sulfosuccinates), the sulfates, and the sulfonates, including, for example, alkaline salts of alkyl sulfates. In some embodiments, no anionic surfactant is used.

Among embodiments in which one or more cationic surfactant is used, some suitable cationic surfactants include, for example, amine surfactants and quaternary ammonium salt surfactants. In some embodiments, no cationic surfactant is used.

In some embodiments, one or more nonionic surfactant is used. Among embodiments in which one or more nonionic surfactant is used, some suitable nonionic surfactants include, for example, fatty ethoxylates, fatty acid esters of polyhydroxy compounds, amide oxides, alkyl oxide block copolymers, silicone based nonionic surfactants, fluorosurfactants, and mixtures thereof.

Suitable fatty ethoxylates include, for example, ethoxylates of fatty alcohols, ethoxylates of fatty acids, ethoxylates of fatty ethanolamides, and ethoxylates of fatty amines. Suitable ethoxylates of fatty alcohols include, for example, ethoxylates of fatty alcohols that have any combination of the following characteristics: linear or branched; primary or secondary; alkyl or alkyl aryl. In some embodiments, one or more fatty ethoxylate is used that is an aryl alkyl ethoxylate, a fatty alcohol ethoxylate, or a mixture thereof.

Suitable silicone based nonionic surfactants include, for example, those with the formula

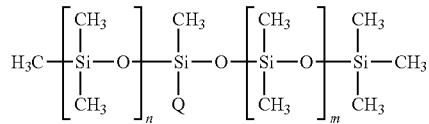

where n is 1 to 5, m is 0 to 4, and Q is

where p is 1 to 6, and q is 3 to 20. In some embodiments, n is 1. Independently, in some embodiments, m is zero. Independently, in some embodiments, p is 3. Independently, in some embodiments, q is 7 or 8 or a mixture thereof. One further example of a suitable nonionic surfactant is Atplus 595. Mixtures of suitable surfactants are also suitable.

Nonionic surfactants may be usefully characterized by HLB, as defined herein above. In some embodiments, one or more nonionic surfactant is used that has HLB of 3 to 4. Independently, in some embodiments, one or more nonionic surfactant is used that has HLB of 8 to 10. In some embodiments, a mixture of surfactants is used that includes one or more nonionic surfactant with HLB of 3 to 4 and also one or more nonionic surfactant with HLB of 8 to 10.

In some embodiments (herein called "continuous oil" embodiments), the continuous medium of the composition of the present invention is the oil medium in which the particles are suspended. In some continuous oil embodiments, one or more surfactant is present in the composition. In some continuous oil embodiments, no surfactant is present in the composition. Independently, in some continuous oil embodiments, little or no water is present; that is, in such embodiments, if any water is present, the amount of water, by weight based on the weight of the composition, 5% or less; or 2% or less; or 1% or less; or 0.5% or less; or 0.1% or less.

In some continuous oil embodiments, the amount of cyclopropene is 1 gram of cyclopropene per liter of oil ("g/L") or more; or 2 g/L or more, or 5 g/L or more, or 10 g/L or more, or 20 g/L or more. Independently, in some continuous oil embodiments, the amount of cyclopropene is 200 g/L or less; or 100 g/L or less; or 50 g/L or less.

In some continuous oil embodiments, the amount of dispersant, by weight based on the weight of the composition, is 0.1% or more; or 0.2% or more; or 0.5% or more, or 0.75% or more. Independently, in some continuous oil embodiments, the amount of dispersant, by weight based on the weight of the composition, is 20% or less; or 10% or less; or 5% or less; or 2% or less.

In some continuous oil embodiments, the amount of surfactant, by weight based on the weight of the composition, is 0.5% or more; or 1% or more, or 2% or more. Independently in some continuous oil embodiments, the amount of surfactant, by weight based on the weight of the composition, is 20% or less; or 10% or less. In some continuous oil embodiments, no surfactant is present.

In some continuous water embodiments, one or more surfactant is present in the composition. In some continuous water embodiments, one or more nonionic surfactant is present in the composition. In some continuous water embodiments, one or more nonionic surfactant with HLB of 3 to 4 is present in the composition, and one or more surfactant with HLB of 8 to 10 is also present in the composition. In some embodiments, the choice of one or more surfactant is made because that surfactant is well suited to emulsify the droplets of the specific oil that is used as the oil medium in that embodiment.

In some continuous water embodiments, the amount of cyclopropene, by weight based on the weight of the composition, is 10 parts per million (ppm) or greater; or 20 ppm or greater; or 50 ppm or greater. Independently, in some continuous water embodiments, the amount of cyclopropene, by weight based on the weight of the composition, is 500 ppm or lower; or 200 ppm or lower.

In some continuous water embodiments, the amount of dispersant, by weight based on the weight of the composition, is 2.5 ppm or greater; or 10 ppm or greater; or 50 ppm or greater; or 200 ppm or greater. Independently, in some continuous water embodiments, the amount of dispersant, by weight based on the weight of the composition, is 1250 ppm or lower; or 1000 ppm or lower, or 750 ppm or lower.

In some continuous water embodiments, the amount of surfactant, by weight based on the weight of the composition, is, by weight of dry surfactant based on the weight of the composition, 0.02% or more, or 0.05% or more, or 0.1% or more, or 0.2% or more. Independently, in some continuous water embodiments, the amount of surfactant, by weight based on the weight of the composition, is, by weight of dry surfactant based on the weight of the composition, 2% or less, or 1% or less, or 0.5% or less.

The composition of the present invention may be made by any method. In some suitable methods, the starting materials are oil, dispersant, optional surfactants, and cyclopropene complex. In some embodiments, the cyclopropene complex starting material is in the form of powder particles that contain cyclopropene complex, and the powder particles have median size, as measured by the largest dimension, much larger than 50 micrometer (for example, 200 micrometer or larger). In some embodiments, the starting materials may be put into a media mill and then milled until the desired particle size is obtained. In some embodiments, the milling process is performed until the particles have median size, as measured by the largest dimension, of 50 micrometer or smaller, or 20 micrometer or smaller, or 10 micrometer or smaller, or 5 micrometer or smaller, or 2 micrometer or smaller.

In some embodiments involving milling, the mixture that is milled contains cyclopropene complex powder in an amount, by weight based on the weight of the mixture that is milled, of 2% or greater; or 5% or greater; or 10% or greater; or 20% or greater. Independently, in some embodiments involving milling, the mixture that is milled contains cyclopropene complex powder in an amount, by weight based on the weight of the mixture that is milled, of 60% or lower; or 50% or lower.

In some embodiments involving milling, the mixture that is milled contains dispersant in an amount, by weight based on the weight of the mixture that is milled, of 0.02% or greater; or 0.05% or greater; or 0.1% or greater; or 0.2% or greater; or 0.5% or greater; or 1% or greater. Independently, in some embodiments involving milling, the mixture that is milled contains dispersant in an amount, by weight based on the weight of the mixture that is milled, of 10% or lower; or 7% or lower; or 5% or lower.

In some embodiments involving milling, the mixture that is milled contains surfactant in an amount, by weight based on the weight of the mixture that is milled, of 0.2% or greater; or 0.5% or greater; or 1% or greater. Independently in some embodiments involving milling, the mixture that is milled contains surfactant in an amount, by weight based on the weight of the mixture that is milled, of 30% or lower; or 10% or lower; or 6% or lower. In some embodiments involving milling, the mixture that is milled contains no surfactant.

In some embodiments involving milling, the mixture that is milled contains oil in an amount, by weight based on the weight of the mixture that is milled, of 40% or greater; or 50% or greater. Independently, in some embodiments involving milling, the mixture that is milled contains oil in an amount, by weight based on the weight of the mixture that is milled, of 98% or lower; or 80% or lower; or 70% or lower.

In some embodiments involving milling, water is excluded from the starting materials, from the mixture that is milled, and from the milled mixture when it is stored. That is, in such embodiments, the amount of water in the mixture of starting materials, by weight based on the total weight of starting materials, is 2% or less; or 1% or less; or 0.5% or less; or 0.2% or less; or 0.1% or less; or zero. In such embodiments, the same amounts of water are contemplated for the mixture during milling and for the milled mixture when it is stored. The mixture during storage may or may not have higher amount of water than the mixture during milling. Independently, the mixture during milling may or may not have higher amount of water than the mixture of starting materials prior to milling.

The product of such a milling process may be used immediately or may be stored.

When it is desired to practice a continuous oil embodiment, the product of the milling process may be used directly, or further oil may be added to the product of such a milling process.

When it is desired to practice a continuous water embodiment, the product of such a milling process will be divided into droplets and suspended in an aqueous medium. In some embodiments, the product of the milling process may be added to the aqueous medium and subjected to agitation, and the product of the milling process will divide into suspended droplets. In some of such embodiments, one or more surfactant is chosen to assist the product of the milling process to divide and suspend in the aqueous medium, and such surfactant or surfactants are added to the starting materials and included in the mixture that is milled. Whether or not surfactant is included in the mixture that is milled, one or more surfactant may be added, after the milling process is completed, to the product of the milling process, or to the aqueous medium (before or after the aqueous medium is mixed with the product of the milling process).

In general, whenever a cyclopropene complex is used, it is known that direct contact between cyclopropene complex and water sometimes causes release of cyclopropene from the complex earlier than desired, and the cyclopropene may be lost (for example, through diffusion out of the composition, through chemical reaction, or a combination thereof). It is contemplated that, in the practice of continuous water embodiments of the present invention, the cyclopropene complex remains in the oil medium, so that contact between the cyclopropene complex and water is minimized or eliminated, and thus a desirably high fraction of the cyclopropene molecules of the composition remain in the composition.

One possible use for the composition of the present invention is to treat plants or plant parts by bringing composition of the present invention into contact with plants or plant parts. Plants that produce useful plant parts are known herein as "crop plants." Treatment may be performed on growing plants or on plant parts that have been harvested from growing plants. It is contemplated that, in performing the treatment on growing plants, the composition of the present invention may be contacted with the entire plant or may be contacted with one or more plant parts. Plant parts include any part of a plant, including, for example, flowers, buds, blooms, seeds, cuttings, roots, bulbs, fruits, vegetables, leaves, and combinations thereof.

Removal of useful plant parts from crop plants is known as harvesting. In some embodiments, crop plants are treated with composition of the present invention prior to the harvesting of the useful plant parts.

The composition of the present invention may be brought into contact with plants or plant parts by any method, including, for example, spraying, dipping, drenching, fogging, and combinations thereof. In some embodiments, spraying is used.

Suitable treatments may be performed on plants that are planted in a field, in a garden, in a building (such as, for example, a greenhouse), or in another location. Suitable treatments may be performed on a plants that are planted in open ground, in one or more containers (such as, for example, a pot, planter, or vase), in confined or raised beds, or in other places. In some embodiments, treatment is performed on plants that are in a location other than in a building. In some embodiments, plants are treated while they are growing in containers such as, for example, pots, flats, or portable beds.

Many of the plants that are suitable for use in the practice of the present invention can be usefully divided into categories or groups. One useful method for defining such groups is the "Definition and Classification of Commodities," published on or before Mar. 23, 2006, by the Food and Agriculture Organization ("FAO") of the United Nations as a "Draft."

In the practice of some embodiments of the present invention, it is contemplated to use plants that produce one or more crops that fall within any one of the following crop groups.

Crop Group 1 is cereals, including, for example, wheat, rice, barley, corn, popcorn, rye, oats, millet, sorghum, buckwheat, quiona, fonio, triticale, canary seed, canagua, quihuicha, adlay, wild rice, and other cereals. In some embodiments of the present invention, suitable plants are those that produce wheat or rice or corn or sorghum. In some embodiments, corn plants are suitable. In some embodiments, wheat plants are suitable. Crop Group 2 is roots and tubers.

Crop Group 3 is sugar crops, including, for example, sugar cane, sugar beet, sugar maple, sweet sorghum, sugar palm, and other sugar crops. Crop Group 4 is pulses, including, for example, beans, chickpea, garbanzo, blackeyed pea, pigeon pea, lentil, and other pulses. Crop Group 5 is nuts, including, for example, brazil nuts, cashew nuts, chestnuts, almonds, walnuts, pistachios, hazelnuts, pecan nut, macadamia nut, and other nuts.

Crop Group 6 is oil-bearing crops, including, for example, soybeans, groundnuts (including peanuts), coconuts, oil palm fruit, olives, karite nuts, castor beans, sunflower seeds, rapeseed, canola, tung nuts, safflower seed, sesame seed, mustard seed, poppy seed, melonseed, tallowtree seeds, kapok fruit, seed cotton, linseed, hempseed, and other oilseeds. In some embodiments, soybean plants are suitable.

Crop Group 7 is vegetables, including, for example, cabbages, artichokes, asparagus, lettuce, spinach, cassava leaves, tomatoes, cauliflower, pumpkins, cucumbers and gherkins, eggplants, chilies and peppers, green onions, dry onions, garlic, leek, other alliaceous vegetables, green beans, green peas, green broad beans, string beans, carrots, okra, green corn, mushrooms, watermelons, cantaloupe melons, bamboo shoots, beets, chards, capers, cardoons, celery, chervil, cress, fennel, horseradish, marjoram, oyster plant, parsley, parsnips, radish, rhubarb, rutabaga, savory, scorzonera, sorrel, watercress, and other vegetables.

Crop Group 8, is fruits, including, for example, bananas and plantains; citrus fruits; pome fruits; stone fruits; berries; grapes; tropical fruits; miscellaneous fruits; and other fruits. Crop Group 9 is fibers, including, for example, cotton, flax, hemp, kapok, jute, ramie, sisal, and other fibers from plants. In some embodiments, cotton plants are suitable. Crop Group 10 is spices. Crop Group 11 is Fodder crops. Fodder crops are crops that are cultivated primarily for animal feed. Crop Group 12 is stimulant crops, including, for example, coffee, cocoa bean, tea, mate, other plants used for making infusions like tea, and other stimulant corps.

Crop Group 13 is tobacco and rubber and other crops, including, for example, plant oils used in perfumery, food, and other industries, pyrethrum, tobacco, natural rubber, natural gums, other resins, and vegetable waxes.

In some embodiments, the present invention involves treatment of any non-citrus plant (i.e., any plant that is not in the genus Citrus). In other embodiments, the practice of the present invention is limited to the treatment of non-citrus plants. Independently, in some embodiments, all the plants that are treated are not members of the genus *Nicotiana*.

In some embodiments, the composition of the present invention is used to treat crop plants growing in a field. Such a treatment operation may be performed one time or more than one time on a particular group of crop plants during a single growing season. In some embodiments, the amount of cyclopropene used in one treatment is 0.1 gram per hectare (g/ha) or more; or 0.5 g/ha or more; or 1 g/ha or more; or 5 g/ha or more; or 25 g/ha or more; or 50 g/ha or more; or 100 g/ha or more. Independently, in some embodiments, the amount of cyclopropene used in one spraying operation is 6000 g/ha or less; or 3000 g/ha or less; or 1500 g/ha or less. Also contemplated are embodiments in which harvested plant parts are treated.

In some embodiments, the composition of the present invention includes one or more metal-complexing agents. A metal-complexing agent is a compound that contains one or more electron-donor atoms capable of forming coordinate bonds with a metal atoms. Some metal-complexing agents are chelating agents. As used herein, a "chelating agent" is a compound that contains two or more electron-donor atoms that are capable of forming coordinate bonds with a metal atom, and a single molecule of the chelating agent is capable of forming two or more coordinate bonds with a single metal atom. In some embodiments, one or more chelating agent is used. In some embodiment, no metal-coordinating agent is used that is not a chelating agent.

In embodiments in which one or more chelating agent is used, suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis(hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

The use of metal-complexing agent in the present invention is optional. In some continuous water embodiments, one or more metal-complexing agent is used. In some continuous water embodiments, no metal-complexing agent is used. In some continuous oil embodiments, no metal-complexing agent is used.

It is to be understood that for purposes of the present specification and claims that, unless specifically stated otherwise, when a value is stated to be "from X to Y," it is meant that that value is X or greater and also is Y or less.

It is to be understood that for purposes of the present specification and claims that, unless specifically stated otherwise, when a compound is described as a result of a particular chemical reaction, such a description is intended to describe the structure of the compound, whether or not the compound is actually made by performing that particular chemical reaction. For example, an "ethoxylate of a fatty alcohol" is a compound whose structure can be understood by envisioning an ethoxylation process performed on a fatty alcohol, and such a compound may be made by a process of ethoxylation of a fatty alcohol or may be made by a different process.

It is to be understood that for purposes of the present specification and claims that, unless specifically stated otherwise, operations are performed at 25° C. at one atmosphere of pressure in air.

It is to be understood that for purposes of the present specification and claims that the range and ratio limits recited herein can be combined. For example, if ranges of 60 to 120 and 80 to 110 are recited for a particular parameter, it is understood that the ranges of 60 to 110 and 80 to 120 are also contemplated. As a further, independent, example, if a particular parameter is disclosed to have suitable minima of 1, 2, and 3, and if that parameter is disclosed to have suitable maxima of 9 and 10, then all the following ranges are contemplated: 1 to 9, 1 to 10, 2 to 9, 2 to 10, 3 to 9, and 3 to 10.

Thickeners that can be incorporated into the suspension compositions provided include those components that thicken or increase viscosity of the composition. Thickeners that can be used in the suspension compositions provided include those components referred to in the art as viscosity controlling agents.

Examples of thickeners include cellulose-based thickeners, for example hydroxyethyl cellulose, methylcellulose, hydroxypropyl cellulose and carboxymethyl cellulose. Other examples of thickeners include cellulose gum, alkane triols; acrylates; substituted celluloses such as hydroxy ethyl cellulose, carboxymethyl cellulose, methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. Additional suitable thickeners include organoclays, which can be made from natural smectite, hectorite or montmorillonite clays by reacting the hydrophilic clay with quaternary ammonium compounds, so that it becomes organophilic and therefore compatible with non-aqueous media.

In one embodiment, suitable thickeners include polymeric thickener which is an addition polymer of unsaturated carboxylic acids and/or anhydrides. Examples of polymeric thickeners include polyacrylates, polyalkylacrylates, polymethacrylate, and maleic anhydride. These polymeric thickeners may have an average molecular weight range from about 500,000 to about 2 millions; or 1 million to 4 millions.

In another embodiment, suitable thickeners include copolymers of acrylates and methacrylates, or copolymers of acrylic acid and alkylmethacrylate, for example, as disclosed in U.S. Pat. No. 5,373,044 and US published application US2009/0253862 A, the contents of which are hereby incorporated by reference. The suspension composition provided can have a viscosity of from about 50 to about 50,000 mPas; or 500 to 15,000 mPas.

Suitable polymeric thickener can be selected from the group consisting of natural rubber, polypropylene, polyisoprene, polybutadiene, poly(styrene-butadiene), poly(ethylene-propylene-diene), polyurethane, polymethacrylate, polyisobutylene, poly(isobutylene-succinic acid), poly(isobutylene-succinic acid-polyacrylamide), polyurea and polyethylene. In some embodiments, the polymeric thickener comprises a first component and a second component, with the first component having a higher weight average molecular weight than the second component. For example, the polymeric thickener comprises a high molecular weight component and a low molecular weight component, characterized in that the thickener comprises a mixture of (1) a (co- or homo-)polymer of propylene with a weight average molecular weight of more than 200.000 and (2) a (co- or homo-)polymer of propylene with a weight average molecular weight of less than 200.000.

In another embodiment, the polymeric thickener comprises a high molecular weight component comprising a (co- or homo-)polymer of propylene with a weight average molecular weight of at least 200.000, or 200.000-350.000, and a low molecular weight component comprising a (co- or homo-) polymer of propylene with a weight average molecular weight of less than 100.000, or 50.000-100.000. The weight ratio between the high molecular weight component and the low molecular weight component in the polymeric thickener can be 1:40-3:1; 1:40-1:1; 1:40-1:5; 1:25-1:15; or 1:18-1:20.

In one embodiment, the low molecular weight component comprises a polypropylene homopolymer, or a polypropylene homopolymer with a melt flow rate of 500-1500 dg/min., or 750-1250 dg/min. as determined by test ASTM D 1238 L. In a further or alternative embodiment, the low molecular weight component comprises a polypropylene homopolymer. In another embodiment, the high molecular weight component has a melt flow rate (ASTM D-1238) of 1.5-15; 1.5-7; or 3-5. In a further or alternative embodiment, the high molecular weight component comprises a polypropylene homopolymer or a propylene/ethylene-copolymer.

In another aspect, provided is a composition comprising an oil medium, wherein particles are suspended in said oil medium, wherein said particles comprise cyclopropene and molecular encapsulating agent, and wherein said particles have median size, as measured by the largest dimension, of 50 micrometer or less.

In one embodiment, said oil medium comprises one or more dispersant. In another embodiment, said oil medium comprises one or more nonionic surfactant. In another embodiment, said oil medium comprises one or more nonionic surfactant with HLB value of 3 to 4 and one or more nonionic surfactant with HLB value of 8 to 10. In another embodiment, said oil medium is in the form of droplets suspended in water. In another embodiment, said oil medium forms the continuous medium of said composition. In another embodiment, said particle have median aspect ratio of 20 or less.

In another aspect, provided is a process for treating plants or plant parts comprising contacting the composition provided herein with said plants or plant parts. In another aspect, provided is a process for forming a composition, said process comprising making a mixture comprising cyclopropene complex, oil, and dispersant to a media mill; and milling said mixture to form particles that comprise said cyclopropene complex, wherein said particles have median size, as measured by the longest length, of 300 micrometer or less, of 200 micrometer or less, or of 50 micrometer or less.

In another aspect, provided is a composition comprising solid particles of a cyclopropene complex comprising a cyclopropene molecular or a portion of a cyclopropene molecular encapsulated in a molecular encapsulating agent, characterized in that said composition additionally comprises an oil medium that said solid particles are suspended in said oil medium, and that said solid particles have a median size, as measured by the largest dimension, of 50 micrometer or less.

In one embodiment, said oil medium comprises one or more dispersant. In another embodiment, said molecular encapsulating agent is alpha-cyclodextrin, beta-cyclodextrin, gamma-cyclodextrin, or a mixture thereof. In another embodiment, said cyclopropene molecule has a structure of formula

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_1$-8 alkyl. In another embodiment, R is methyl.

In another embodiment, said cyclopropene molecule has a structure of formula:

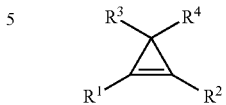

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen. In a further embodiment, the cyclopropene comprises 1-methylcyclopropene (1-MCP).

In another embodiment, said oil medium comprises one or more nonionic surfactant. In another embodiment, said oil medium comprises one or more nonionic surfactant with HLB value of 3 to 4 and one or more nonionic surfactant with HLB value of 8 to 10. In another embodiment, said oil medium is in the form of droplets suspended in water. In another embodiment, said oil medium forms the continuous medium of said composition. In another embodiment, said particle have median aspect ratio of 20 or less.

In another aspect, provided is a process for treating plants or plant parts comprising contacting the composition provided herein with said plants or plant parts.

In another aspect, provided is a process for forming a composition, said process comprising placing materials comprising cyclopropene complex, oil, and dispersant into a media mill; and milling said mixture to form solid particles that comprise said cyclopropene complex, wherein said solid particles have median size, as measured by the longest length, of 50 micrometer or less; wherein said cyclopropene complex comprising a cyclopropene molecule or a portion of a cyclopropene molecule encapsulated in a molecular encapsulating agent;

In one embodiment, said oil medium comprises one or more dispersant. In another embodiment, said molecular encapsulating agent is alpha-cyclodextrin, beta-cyclodextrin, gamma-cyclodextrin, or a mixture thereof. In another embodiment, said cyclopropene molecule has a structure of formula

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In another embodiment, said cyclopropene molecule has a structure of formula:

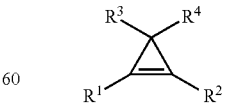

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen. In a further embodiment, the cyclopropene comprises 1-methylcyclopropene (1-MCP).

EXAMPLES

The materials used in the following Examples were these:

Complex 1=Dry powder containing complex of 1-MCP and alpha-cyclodextrin, contains 3.8% 1-MCP by weight. Median size, measured by the longest dimension, is greater than 100 micrometer. Median aspect ratio is over 50.

Oil P1=paraffin oil containing aryl alkyl ethoxylate surfactant, from Whitmire Micro-Gen Company Oil P2=paraffin oil, from Petro Canada Company Brij™ 30=surfactant: (ethylene oxide)$_4$ lauryl ether, from Croda (HLB 9.7)

Silwet™ L-77=surfactant: nonionic silicone from OSi Specialties (HLB 5 to 8)

Atlox™ 4914=dispersant: block copolymer of poly(ethylene oxide) and alkyd resin, from Croda (HLB 6)

EDTA=ethylenediamine tetraacetic acid, sodium salt

Atsurf™ 595=surfactant: glycol mono oleate from Croda Company (HLB 3.8)

Dyne-Amic™ oil=blend of highly refined methylated vegetable oils in combination with organosilicone-based surfactants. from Helena Chemicals Oil Emulsion 1=0.38 parts by weight Dyne-Amic™ oil added to 99.62 parts by weight water, and agitated Rizo™ Oil=emulsifiable methylated soybean oil, from Rizo bacter Company SoyGold™ 1100=methylated soybean oil, from Ag Environmental Products Company

Example 1

Formation of Formulation B

The following ingredients were added to a media mill:
292.4 g of Oil P1
102.0 g of Complex 1
5.6 g of Atlox™ 4914

The mixture of ingredients was processed in the media mill until median particle size, as measured by the largest dimension, was less than 2 micrometers.

Example 2

Formation of Formulation C

The following ingredients were added to a media mill:
194.2 g of Oil P2
175.0 g of Complex 1
6.0 g of Brij™ 30
18.0 g of Silwet™ L-77
6.8 g of Atlox™ 4914

The mixture of ingredients was processed in the media mill until median particle size, as measured by the largest dimension, was less than 2 micrometers.

Example 3

Formation of Formulation D

The following ingredients were added to a media mill:
200.4 g of SoyGold 1100
180.0 g of Complex 1
10.0 g of Silwet™ L-77
4.0 g of Atlox™ 4914
5.6 g of EDTA The mixture of ingredients was processed in the media mill until median particle size, as measured by the largest dimension, was less than 2 micrometers.

Example 4

Retention of 1-MCP

The ability of a formulation to retain 1-MCP was assessed by spraying the spray mixture through a standard spray nozzle, collecting the spray liquid at the spray nozzle and at 46 cm (18 inches) from the nozzle, and analyzing for 1-MCP by capturing the collected liquid in a closed container and analyzing the headspace gas by gas chromatography. Gas chromatography of the headspace was performed as described in US Patent Publication 2005/0261132. The initial and final unsprayed portion is also analyzed to determine the amount lost to spraying and the amount lost to headspace during the spraying operation.

Spray Formulation "Comparative SF-A4" was a mixture of Oil Emulsion 1 and Complex 1. Spray Formulation "SF-B4" was Formulation B, added to water. Each Spray formulation contained 100 mg/L 1-MCP and was sprayed through Tee-Jet™ XR8002VS nozzles at 138 kPa (20 psi) pressure. The results are shown in Table 1:

TABLE 1

| Spray Composition | MCP concentration (% of concentration in initial unsprayed formulation) | | |
|---|---|---|---|
| | at nozzle | 46 cm from nozzle | final unsprayed portion |
| Comparative SF-A1 | 58 | 33 | 75 |
| SF-B | 75 | 74 | 99 |

Table 1 shows that the oil formulation performs much better than the tank mix of 1-MCP complex and oil and also helps keep the 1-MCP in the unsprayed spray liquid.

Example 5

Biological Efficacy

Efficacy of formulations was assessed by spraying greenhouse tomato plants, exposing them to ethylene, and evaluating the resistance to epinastic (i.e., leaf bending/curling) response specifically caused by ethylene.

The 1-MCP treated plants and the controls were placed into an SLX controlled-atmosphere shipping box and sealed. To the box, ethylene was injected through a septum, which gave a concentration of 14 ppm. The plants were held sealed for 12-14 hours in the dark with ethylene in the atmosphere. At the end of ethylene treatment, the box was opened and scored for epinasty. The results are reported as leaf angle relative to the stem wherein a value of 50 degrees is typical of an unaffected leaf and 120 degrees is one fully bent by the action of ethylene.

Spray Formulation "Comparative SF-A51" was 99.99 parts by weight of Oil Emulsion 1 plus 0.0132 parts by weight of Complex 1. Comparative SF-A2 was sprayed on the plants to give a rate of 1 g 1-MCP/Ha. Spray Formulation "Comparative SF-A52" was 99.17 parts by weight of Oil Emulsion 1 plus 0.132 parts by weight of Complex 1. Comparative SF-A2 was sprayed on the plants to give a rate of 10 g 1-MCP/Ha.

Spray Formulation "SF-C51" was 0.0279 parts by weight of Formulation C plus 99.97 parts by weight of water. SF-C51 was sprayed on the plants to give a rate of 1 g 1-MCP/Ha. Spray Formulation "SF-C52" was 0.279 parts by weight of Formulation C plus 99.72 parts by weight of water. SF-C52 was sprayed on the plants to give a rate of 10 g 1-MCP/Ha.

TABLE 2

Results of spray formulations

| Composition | 1-MCP g/Ha | Leaf Angle |
|---|---|---|
| untreated, unexposed to ethylene | 0 | 52° |
| Oil Emulsion 1 | 0 | 116° |
| water | 0 | 116° |
| Comparative SF-A51 | 1 | 119° |
| SF-C51 | 1 | 87° |
| Comparative SF-A52 | 10 | 82° |
| SF-C52 | 10 | 54° |

Leaf angles demonstrate that the oil formulations SF-C51 and SF-C52 are more effective at counteracting the effects of ethylene than the comparative formulations.

Example 6

Crop Yield Increase

Efficacy of formulations was assessed in field applications on soybeans. The measure of efficacy was yield increase.

Spray Formulation "Comparative SF-A6" was made as follows. 98.97 parts by weight of water was mixed in the spray tank with 1 part by weight of Rizo™ Oil, and then 0.0329 parts by weight of Complex 1 was mixed with the mixture in the spray tank. The spraying rate was chosen to give 25 g 1-MCP/Ha in 200 L/Ha water containing 2 L/Ha of Rizo™ Oil. Comparative SF-A6 was applied by ground-level spray.

Sprayable Formulation SF-D6 was made by mixing 1.25 liter of Formulation D with 3.75 liter of Rizo™ Oil. Sprayable Formulation SF-D6 was applied by aerial spraying at rate of 25 g 1-MCP/Ha in 5 L total oil/Ha. Note: no water was used in SF-D6, so the total liquid spray volume was 5 L/Ha. Results are shown in Table 3. Yield is reported as a percentage of the yield obtained from the untreated control.

TABLE 3

Results for crop yield increase

| Spray Treatment | Soybean Yield |
|---|---|
| Comparative SF-A6 | 103% |
| SF-D6 | 110% |

SF-D6 increased soybean yield significantly more than the Comparative formulation.

Example 7

Suspension Composition Comprising Kraton G1702H

Kraton G1702H is a linear styrene ethylene/propylene diblock copolymer. 100 g of Kraton G1702H is mixed with 1900 g of Isopar V and heated with stirring to 100° C. for 30 minutes. A clear viscous liquid is formed with 5% solids.

Similarly a more viscous, but still pourable, liquid can be formed with 8% Kraton G1702H in Isopar V. These concentrated solutions can be diluted with additional solvent by simple mixing at room temperature.

Especially useful viscosities are found at 2.25% and 2.50% Kraton G1702H in solvent. Kraton G1702H has also can be dissolved at similar concentrations in (1) white mineral oils including Blandol and Klearol; (2) hydrotreated middle petroleum distillates including Conosol 260, Unipar SH 260 CC, Isopar V Fluid; and (3) hydrotreated light petroleum distillates such as Unipar SH 210 AS, Isopar M Fluid. Each of the above compositions can yield solutions with increased viscosity. Vegetable oils, including soybean oil and corn oil, do not exhibit this effect. When 1-methylcyclopropene/α-cyclodextrin complex and/or zeolite/molecular sieve are suspended in the thickened hydrocarbons, little or no settling occurs if the concentration of Kraton G1702H is greater than 2.0% by weight. In addition, a suspension of 10% by weight of 1-methylcyclopropene/α-cyclodextrin complex and 3.3% by weight of Siliporite NK10AP (4A molecular sieve) in 2.25% Kraton G1702H is directly sprayable using traditional spray nozzles (Spraying Systems TeeJet XR8002 or XR8008) using a normal pressure of 30 psig to 60 psig.

Polymers not suitable as thickeners include: (1) Nordel IP3745P—an ethylene propylene norbornadiene terpolymer: 100 g of Nordel IP3745 is mixed with 1900 g of Isopar V and heated, with stirring, to 100° C. for 4 hours. None seems to dissolve and no thickening is noted; (2) Septon 1020—a linear styrene ethylene/propylene diblock copolymer: 100 g of Septon 1020 is mixed with 1900 g of Isopar V and heated, with stirring, to 100° C. for 4 hours. Only a little dissolved but only minor thickening is noted; and (3) Septon 1001—a linear styrene ethylene/propylene diblock copolymer: 100 g of Septon 1001 is mixed with 1900 g of Isopar V and heated, with stirring, to 100° C. for 4 hours. Only a little dissolved but some (but insufficient) thickening is noted.

We claim:

1. A composition comprising solid particles of a cyclopropene complex comprising a cyclopropene molecule encapsulated in a molecular encapsulating agent, characterized in that said composition additionally comprises an oil medium, that said solid particles are stably suspended in said oil medium, and that said solid particles have a median size, as measured by the largest dimension, of 50 micrometer or less;

wherein said oil medium comprises one or more dispersants;

wherein said molecular encapsulating agent is alpha-cyclodextrin, beta-cyclodextrin, gamma-cyclodextrin, or a mixture thereof; and wherein said cyclopropene molecule has a structure of formula where each of $R^1$, $R^2$, $R^3$, and $R^4$ is hydrogen or $(C_1\text{-}C_4)$ alkyl.

2. The composition of claim 1, wherein said cyclopropene molecule is 1-MCP.

3. The composition of claim 1, wherein said oil medium comprises one or more nonionic surfactant.

4. The composition of claim 1, wherein said oil medium comprises one or more nonionic surfactant with HLB value of 3 to 4 and one or more nonionic surfactant with HLB value of 8 to 10.

5. The composition of claim 1, wherein said oil medium is in the form of droplets suspended in water.

6. The composition of claim 1, wherein said oil medium forms a continuous medium of said composition.

7. The composition of claim 1, wherein said particle have median aspect ratio of 20 or less.

8. A process for treating plants or plant parts comprising contacting said plants or plant parts with the composition of claim 1.

9. A process for forming a composition, said process comprising:
   placing materials comprising a cyclopropene complex and an oil into a media mill;
   milling said materials to form solid particles that comprise said cyclopropene complex,
   wherein said solid particles have median size, as measured by the longest length, of 50 micrometer or less; and
   stably suspending said solid particles in said oil;
   wherein said oil comprises one or more dispersants;
   wherein said cyclopropene complex comprises a cyclopropene molecule encapsulated in a molecular encapsulating agent;
   wherein said molecular encapsulating agent is alpha-cyclodextrin, beta-cyclodextrin, gamma-cyclodextrin, or a mixture thereof; and
   wherein said cyclopropene molecule has a structure of formula

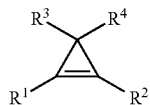

where each of $R^1$, $R^2$, $R^3$, and $R^4$ is hydrogen or $(C_1-C_4)$ alkyl.

10. The process of claim 9, wherein said cyclopropene molecule is 1-MCP.